United States Patent [19]

Kink et al.

[11] Patent Number: 5,747,240
[45] Date of Patent: May 5, 1998

[54] EPITOPE MAPPING OF THE C33 REGION OF HCV

[76] Inventors: John A. Kink, 1454 Carriage La., Lake Villa, Ill. 60046; Terence E. Ryan, 234 Florence Ct., Libertyville, Ill. 60048; John A. Todd, 212 Mainsail Dr., Grayslake, Ill. 60030; Badr Saeed, 205 Bingham Cir., Mundelein, Ill. 60060

[21] Appl. No.: 411,913

[22] Filed: Mar. 28, 1995

Related U.S. Application Data

[63] Continuation of Ser. No. 972,061, Nov. 5, 1992, abandoned, which is a continuation of Ser. No. 789,093, Nov. 7, 1991, abandoned.

[51] Int. Cl.$^6$ .................. C12Q 1/70; G01N 33/53; G01N 33/551; C07K 14/18
[52] U.S. Cl. .................. 435/5; 435/7.1; 435/7.92; 530/350
[58] Field of Search ................. 530/350; 435/5, 435/7.1, 7.92

[56] References Cited

U.S. PATENT DOCUMENTS 5,350,671  9/1994  Houghton et al. .................. 435/5

FOREIGN PATENT DOCUMENTS

| 318216 | 5/1931 | European Pat. Off. . |
|---|---|---|
| 0388232 | 9/1990 | European Pat. Off. . |
| 0398748 | 11/1990 | European Pat. Off. . |

OTHER PUBLICATIONS

Ivan M. Roitt "Essential Immunology", 1980, pp. 144–149.
Sambrook et al. "Molecular Cloning: A Laboratory Manual" 2nd Ed. 1989, pp. 18.64–18.66 and 18.70–18.75.
Bradley et al., J. Med. Virol. 3:253 (1979).
Choo et al., Science, 244:359(1989).
Chonczynski and Sacchi, Anal. Biochem., 162:156(1987).
Wang et al., PNAS, 86:9717(1989).
Vogelstein, Anal. Biochem., 160:115(1987).
Mierendorf et al., Methods Enzymol., 152:458(1987).
Saiki et al., Nature, 324:163(1986).
Saiki et al. Science, 239:487(1988).
Dretzen et al., Anal. Biochem., 112:295 (1981).
Birnhoim and Doly, Nucleic Acids Res., 7:1513 (1979).
Laemmli, Nature, 227:680(1970).
Studier and Moffatt, J. Mol. Biol. 189:113(1986).
Smith and Johnson, Gene, 67:31(1988).

Primary Examiner—David Guzo
Attorney, Agent, or Firm—Cynthia G. Tymeson

[57] ABSTRACT

An assay for detection of serum antibodies having specificity to hepatitis C viral antigens utilizes the carboxy-terminal 102 amino acids of the c33c region of nonstructural gene 3 of HCV containing substantially all the epitopes of the gene 3 protein. In the preferred embodiment the recombinant 102 amino acid peptide is coated onto a solid support, and incubated in the presence of serum obtained from a patient infected with HCV. The presence of antibodies bound to the antigen coated support is detected in a sandwich format utilizing a second reporter-conjugated antibody.

10 Claims, 3 Drawing Sheets

FIG. 2

```
  1 GTCACTGTGCCCCATCCCAACATCGAGGAGGTTGCTCTGTCCACCACCGGAGAGATCCCT    60
    ----+----+----+----+----+----+----+----+----+----+----+----+
  1  V  T  V  P  H  P  N  I  E  E  V  A  L  S  T  T  G  E  I  P    20

61 TTTTACGGCAAGGCTATCCCCCTCGAAGTAATCAAGGGGGGAGACATCTCATCTTTCTGT   120
    ----+----+----+----+----+----+----+----+----+----+----+----+
 21  F  Y  G  K  A  I  P  L  E  V  I  K  G  G  R  H  L  I  F  C    40

121 CATTCAAAAGAAGAAGTGCGACGAACTCGCTGCAAAGCTGGTTGCTTTGGGCATCAATGCC   180
    ----+----+----+----+----+----+----+----+----+----+----+----+
 41  H  S  K  K  K  C  D  E  L  A  A  K  L  V  A  L  G  I  N  A    60

181 GTGGCTTACTACCGCGGTCTTGACGTGTCCGTCATCCCGACCAGCGGCGATGTTGTCGTC   240
    ----+----+----+----+----+----+----+----+----+----+----+----+
 61  V  A  Y  Y  R  G  L  D  V  S  V  I  P  T  S  G  D  V  V  V    80

241 GTGGCAACCGATGCCCTCATGACCGGCTATACCGGGGACTTCGACTCGGTGATAGACTGC   300
    ----+----+----+----+----+----+----+----+----+----+----+----+
 81  V  A  T  D  A  L  M  T  G  Y  T  G  D  F  D  S  V  I  D  C   100

301 AATACG   306
    ------
101  N  T   102
```

1

EPITOPE MAPPING OF THE C33 REGION OF HCV

This is a continuation of application Ser. No. 07/972,061 filed on Nov. 5, 1992, now abandoned, which is a continuation of application Ser. No. 7/789,093, filed on Nov. 7, 1991, now abandoned.

BACKGROUND OF THE INVENTION

Although Koch's postulates for definitive identification of the causative agent of non-A non-B hepatitis have not been satisfied, there is general agreement that the hepatitis C virus (HCV) is implicated as a major etiological agent in the disease. The HCV genome is organized like a flavivirus with a single open reading frame containing N-terminal structural genes for capsid, matrix, and envelope, and carboxy-oriented nonstructural genes. The nucleotide and corresponding amino acid sequences for the nonstructural genes are disclosed in EP 0 318 216 (Houghton). Further sequences including those for the structural genes are disclosed in EP 0 388 232 and EP 0 398 748.

Among the HCV proteins of diagnostic interest is the nonstructural gene 3 product, NS3 encompassing amino acid residues approximately 1050 to 1640. Of particular interest is a region known as c33c, contained within NS3, encompassing amino acid residues 1192 to 1457, heretofore disclosed to have potential value in immune assays because of the presence of antigenic determinants to which individuals may develop diagnostically detectable antibodies.

SUMMARY OF THE INVENTION

In developing immune responses in viral infection, it is to be expected that the earliest and usually strongest responses are elicited to the structural proteins, since the these molecules are generally exposed to the cells of the immune system in the course of intercellular proliferation. Thus, it would be expected that the major epitopes of HCV would be contained in the capsid, matrix, and envelope proteins.

Screening of large panels of sera from patients presenting non-A non-B hepatitis, however, revealed a significant number which reacted only to nonstructural gene products. In particular, some sera were positive only to the NS3 partial gene product obtained as a beta-galactosidase-c33c fusion product by polymerase chain reaction (PCR) amplification and cloning into a λgt11 library.

To develop an improved immunoassay utilizing derivatives of c33c, various constructs of portions of the c33c sequence were obtained and tested. Surprisingly, it was discovered that the immunodominant epitopes found in the entire c33c region are all contained in the 102 carboxy-terminal amino acids.

In the present invention, a recombinant protein is provided having the antigenic determinants contained in the 102 carboxy-terminal portion of the c33c region of the NS3 gene product. In an alternative embodiment, a synthetic peptide comprising substantially the same sequence is substituted for the recombinant fusion protein.

The recombinant proteins or synthetic peptides having the aforementioned amino acid sequence, or a sequence presenting substantially identical antigenic properties are utilized in an immunoassay comprising the steps of contacting antibodies against HCV contained in a patient serum specimen with a recombinant protein or synthetic peptide contained in the carboxy-terminal 102 amino acids of the c33c fragment of the NS3 gene product, or a recombinant protein or synthetic peptide having substantially the antigenic determinants of the carboxy-terminal 102 amino acids of the c33c fragment of the HCV NS3 gene product, coated onto a solid support, incubating for a time sufficient to permit binding of antibodies contained in such patient serum specimen which are specific for the c33c fragment, and more specifically, the carboxy-terminal 102 amino acid fragment thereof, or its antigenic equivalent, separating bound from unbound antibodies, and detecting the antibodies so bound.

DESCRIPTION OF DRAWINGS

FIG. 2 (SEQ ID NO: 8 and 9) is the nucleotide and corresponding derived amino acid sequence of a 102 amino acid fragment of NS3.

DETAILED DESCRIPTION OF THE PREFERRED EMBODIMENT

Figure 1:
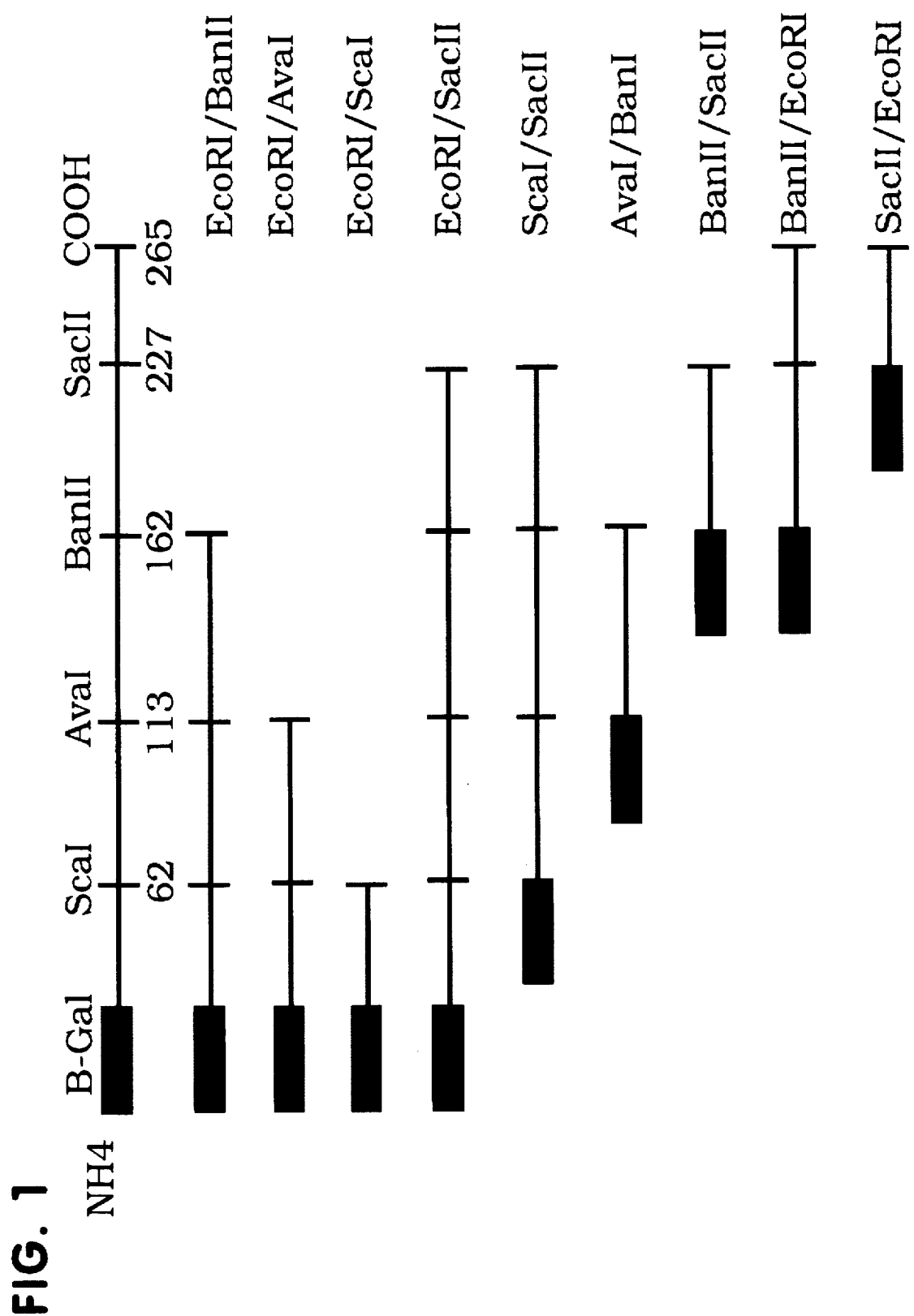
FIG. 1 is a map showing the termini of various fusion proteins obtained from cloning selected restriction fragments.

The c33c fragment of NS3 was cloned from a known HCV source into λgt11 after polymerase chain reaction (PCR) amplification utilizing appropriate primers flanking the c33c region. Thereafter, recombinant c33c fragments were created and expressed in λgt11 and pGEX vectors. The fusion proteins were then transferred onto a solid support, and tested for antigenicity against a panel of HCV antibody containing sera. The details of the molecular cloning and expression of these fusion proteins are set forth in the Examples. By the term c33c, it is meant the 102 amino acid sequence commencing with amino acid 484 (valine) and ending with amino acid 785 (threonine) as depicted in FIG. 15 of EP 0 318 216.

Comparison of fusion proteins containing various lengths of the c33c insert indicated that all positive sera reacted at a comparably high signal to the fragment containing only the last 102 carboxy-terminal amino acids. This means that the immunodominant epitope encoded by the HCV NS3 gene resides in this fragment. This is somewhat surprising in that antigenicity of other proteins has been associated most frequently with the N-terminus of the molecule.

In the assay of the present invention, the recombinant protein is coated onto a solid support, which may be the surfaces of the wells of a conventional microtitre plate. The protein may be covalently attached or passively coated according to conventional procedures. The protein may also be immobilized on a porous tab for assay in a radial partition format, as described in U.S. Pat. No. 4,517,288, Giegel, et al. The protein may also be affixed to a comminuted insoluble matrix such as a cross-linked polystyrene or polyacrylamide which is separable from a liquid phase containing unreacted molecular species by elution, centrifugation, or sedimentation. In the preferred embodiment, the protein is passively coated onto paramagnetic microparticles as described in U.S. patent application, Ser. No. 7/716,144, abandoned, or transferred to Polyvinylidene Difluoride Membrane and nitrocellulose membranes.

In the present assay the solid support as heretofore described, is contacted with a patient specimen in which antibodies may be present which are specific for the coated antigen. The specimen is ordinarily patient serum diluted in buffer, although assay of antibodies from other bodily fluids is possible. The antigen-antibody mixture is incubated at a temperature between 15° and 42° C. for a time sufficient to ensure complete binding of the antibodies to the antigen-coated solid support. This generally takes from about 5 to 30 minutes.

In the separation step which follows the incubation, unbound antibodies remaining in solution are separated from those bound to the antigen-coated solid support, as set forth above. In the case of the paramagnetic particles, the particles are separated by applying a magnetic field to attract the particles into a pellet or to the sides of the reaction vessel in which the assay is conducted. The remaining liquid phase is then aspirated, or otherwise removed by elution or filtration.

Following a wash step in which the solid support is rinsed with buffer, the amount of bound antibody may be measured. Any one of several methods of detection may be selected. For example, a second detecting antibody bearing detection moieties with species specificity to the solid support-bound antibodies may be incubated with the solid support, followed by separation and wash steps as set forth above. The amount of signal generated by the detection moieties is proportional to the amount of antigen-directed antibodies bound to the solid support. Detection moieties may be enzymes conjugated to the detecting antibodies, which act upon a suitable substrate to cause an increase in fluorescence, release of a chromophor, etc. They may be radioactive molecules or atoms, or compounds exhibiting chemiluminescence.

The present antigen also may be utilized in Western blot analyses. According to this method, the antigen is electrophoresed through a 12 percent sodium dodecidium sulfate polyacrylamide gel and transferred to a membrane. The membrane is contacted first with c33c reaction antisera, washed, then contacted with enzyme-conjugated anti-human antisera, and developed with substrate.

In preparing antigens in the form of synthetic peptides, any reliable method of synthesis is contemplated in this invention. A particularly efficacious method of synthesizing the present antigens utilizes a Milligen-Biosearch 9600 model peptide synthesizer using fluoroenylmethoxy carbonyl (FMOC) protection scheme and diisopropylcarbodiimide coupling chemistry. Synthesized peptides may be cleaved from the resin support by Reagent R, which comprises trifluoroacetic acid, thioanisole, ethanedithiol, and anisol in a volumetric ratio of 90:5:3:2.

It will be understood by those skilled in the art, that minor variations in the sequence of the present antigen contained in the 102 amino acid carboxy-terminal fragment of c33c, which do not substantially affect the epitope as a target in the present assay, are the equivalents of the present invention. These variations include small deletions, insertions, or amino acid substitutions. In the preferred embodiment, recombinant proteins are favored over synthetic peptides, because of the difficulty of synthesizing a peptide of 102 amino acids, and because the beta-galactosidave- and Glutathione S-Transterase-derived portions of the fusion protein may confer some stability and accessibility to the antigen, and aids in the purification process.

Further advantages of the present antigen, and a detailed explanation of the identification and use thereof are set forth in the Examples which follow.

EXAMPLE 1

Isolation of HCV c33c Antigen

Plasma from a chimpanzee infected with the prototype strain of HCV, Bradley et al., *J. Med. Virol.*, 3:253 (1979),
and Choo et al., *Science*, 244:359 (1989), was clarified by centrifugation at 15,000×g for 20 minutes at 4° C. Clarified plasma was centrifuged at 78,000×g for 4 hours at 4° C. to pellet HCV virions. The virus pellet was extracted by a guanidinium isothiocyanate-phenol-chloroform method, Chomczynski and Sacchi, *Anal. Biochem.*, 162:156 (1987), and precipitated with ethanol in the presence of glycogen as a carrier co-precipitant. The ethanol precipitate was washed and resuspended in a solution of 1 mM EDTA, 10 mM NaCl, 10 mM Tris, pH 8 prior to reverse transcription.

The c33c region of HCV was amplified using a commercial RNA PCR Kit (Perkin Elmer-Cetus, Norwalk, Conn.) utilizing a c33c-specific oligonucleotide primer for first-strand synthesis, SEQ ID NO:1, (5'-CCGGCCGGCCCAA-TTTCACACGTATTCCAGTCTATCA-3') using Applied Biosystem systems synthesizer using phosphoramidite chemistry. Reverse transcription, Wang et al., *PNAS*, 86:971 (1989), was performed according to the kit instructions, except that the transcription incubation at 42° C. was increased to one hour.

Specifically-primed cDNAs were amplified via the polymerase chain reaction method using a second oligonucleotide primer, SEQ ID NO:2, (5'-CGCGCGCGCGGAATT-CGTGGACTTTATCCCTGTGGA-3'). Forty cycles of amplification with a profile of 94° C., 1 minute; 37° C., 2 minutes; and 72° C., 3 minutes was performed. Amplification products were extracted with phenol/chloroform, precipitated, and digested with restriction enzyme EcoRI to create cohesive ends in the termini. Sambrook et al., *Molecular Cloning: A Laboratory Manual*, Cold Spring Harbor Press, Cold Spring Harbor, N.Y. (1989). The amplified DNAs were then size-fractioned in a 1% agarose gel, and a band of the expected size of c33c (827 bp) was excised, and purified using a CoStar Spin-X filter, Vogelstein, *Anal. Biochem.*, 160:115 (1987). The eluted band was ligated to EcoRI digested, calf intestinal phosphate-treated λgt11 arms (stratagene San Diego, Calif.). Ligated DNAs were introduced into phage heads using a commercially prepared packaging mixture (Giga-Pack Gold II, Stratagene), and phage containing the c33c coding sequences were identified by immunoscreening against human HCV antisera reactive to c33c, as herein after more fully described.

EXAMPLE 2

Immunoscreening of c33c Library

The λgt11 was immunoscreened essentially as described by Mierendorf et al., *Methods Enzymol.*, 152:458 (1987). Plating host bacteria (*E. coli* strain Y1090(r⁻) Stratagene) were prepared as described by Sambrook et al., *Molecular Cloning: A Laboratory Manual*, Cold Spring Harbor Press, Cold Spring Harbor, N.Y. (1989). Cells were grown overnight in LB media containing ampicillin (50 ug/ml), maltose (0.2%) and MgSO₄ (10 mM). The overnight culture was added to fresh LB medium with the above additives and grown to an OD600 of 0.5. The cells were centrifuged and the pellet was resuspended in 0.2 volume of ice-cold 10 mM MgSO₄. The titer of the λgt11 c33c library was determined, Sambrook et al., *Molecular Cloning: A Laboratory Manual*, Cold Spring Harbor Press, Cold Spring Harbor, N.Y. (1989), and 500 to 1000 plaque forming units (pfu) were diluted in 100 ul of SM buffer, Sambrook et al;, *Molecular Cloning: A Laboratory Manual*, Cold Spring Harbor Press, Cold Spring Harbor, N.Y. (1989), and added to 150 ul of the Y1090(r⁻) cell suspension. This suspension was gently mixed, incubated in a 37° C. shaker for 15 minutes, added to 3 ml of top agarose 0.7%, Sambrook et al., *Molecular Cloning: A Laboratory Manual*, Cold Spring Harbor Press, Cold Spring Harbor, N.Y. (1989) and poured onto LB ampicillin plates. The plates were incubated inverted at 42° C. until plaques were visible (about 3 hours). During this time nitrocellulose filters were soaked with 10 mM IPTG (Isopropyl-Beta-D-Thiogalactopyranoside) and allowed to air dry. Once the plaques became visible, the filters were placed on the plates and incubated inverted at 37° C. for an additional 3 hours. The filters were then marked for orientation, rinsed with Tris buffered saline (TBS: 10 mM Tris, 150 mM NaCl, pH 7.4) and incubated with non-fat dry milk solution (NFDM: TBS, 2% non-fat dry milk, 0.1% $NaN_3$) for 15 minutes. Primary antibody was a characterized Serum from Boston Biomedica, Boston, Mass., anti-HCV mixed titer #8 PHV201-08. This serum was strongly reactive and specific to the c33c domain of HCV as determined by Boston Biomedica, RIBA 2 testing, Ortho Diagnostics, Raritan, N.J., primary antibody was incubated with 10×volume of *E. coli* lysate, centrifuged to remove insoluble *E. coli* protein, and diluted in another 10×volume of NFDM. The filters were treated with the 10 ml of the primary antibody dilution (1:100) overnight with gentle rocking at room temperature. Primary antibody was removed and the filters were then washed 6×5 minutes with TBS+0.05% Tween-20 and then treated with alkaline-phosphatase conjugated goat anti-human IgG and IgM (Jackson and Jackson, Westgrove, Pa.) diluted 1:3500 in NFDM. Filters were incubated for 2.5 hours at room temperature, the secondary antibody was removed and the filters were washed as described above. Filters were then rinsed twice for 5 minutes with 50 mM Tris-HCl pH 9.5. Each filter was treated with 10 ml of substrate; to 10 ml of 50 mM Tris-HCl, pH 9.5 add 33 ul 5-Bromo-4-chloro-indolylphosphate of (BCIP, 50 mg/ml DMF) and 44 ul of Nitro blue tetrozolium (NBT, 75 mg/ml 70% DMF Bethesda Research Labs, Gaithersburg, Md.). The reaction was stopped by the removal of substrate and addition of 1% glacial acetic acid solution. Filters were rinsed with water and air dried. Reactive plaques were localized by comparison with corresponding bacteriological plate followed by coring with a pipette. Agarose plugs containing phage were placed in 1 ml of SM buffer containing a drop of chloroform and phage were allowed to elute from the agar plug for at least 4 hours at 4° C. Eluted phage were used as a new inoculum for further rounds of immunoscreening until reactive phage were pure (3 rounds total). Three λgt11 clones identified as c33c-1A, c33c-3A and c33c-4A were further tested serologically by immunoscreening using an anti-HCV panel. This panel consisted of characterized anti-HCV sera known to be reactive for c33c and sera non-reactive to c33c. About 1000 pfu's for each clone were plated and immunoscreened as described in above, except the circular filters from each clone were cut into strips and incubated individually with each specimen. The immunoreactivity profile for each clone is presented in Tables 1 and 2. All of the clones matched the expected reactivity pattern for c33c and negative for c33c non-reactive sera.

TABLE 1

Immunoreactivity Profile of c33c Clones to HCV Unreactive Sera

| Clone | LS1 | LS2 | LS3 | LS4 | LS5 | LS6 | LS7 | LS8 | LS9 | LS10 | LS11 | LS12 | LS13 | LS14 |
|---|---|---|---|---|---|---|---|---|---|---|---|---|---|---|
| λgt11* | – | – | – | – | – | – | – | – | – | – | – | – | – | – |
| c33c 1A | – | – | +ʷ | – | – | – | – | – | – | – | – | – | – | – |
| c33c 3A | – | – | +ʷ | – | – | – | – | – | – | – | – | – | – | – |
| c33c 4A | – | – | +ʷ | – | – | – | – | – | – | – | – | – | – | – |

*λgt11 without insert serves as negative control

TABLE 2

Immunoreactivity profile of c33c Clones to HCV c33c Reactive Sera

| Clone | Mixed 8 | Mixed 14 | Mixed 16 | Low 9 | Low 10 | D 13 | D 22 | PB 2453 |
|---|---|---|---|---|---|---|---|---|
| λgt11 | – | – | – | – | – | – | – | – |
| c33c1A | ++ | ++ | +++ | ++ | +++ | ++ | ++ | +++ |
| c33c3A | ++ | ++ | +++ | ++ | +++ | ++ | ++ | +++ |
| c33c4A | ++ | ++ | +++ | ++ | +++ | ++ | ++ | +++ |

*λgt11 without insert serves as negative control

EXAMPLE 3

Isolation and Sequencing of c33c DNA

Unless stated otherwise the procedures described herein are referenced in Sambrook et al., *Molecular Cloning: A Laboratory Manual*, Cold Spring Harbor Press, Cold Spring Harbor, N.Y. (1989). The putative λgt11 c33c recombinants, c33c-1A, c33c-3A, and c33c-4A were used as a template to isolate the c33c insert by Polymerase Chain Reaction (PCR) Methodology, Saiki et al., *Nature*, 324:163 (1986), and Saiki et al., *Science*, 239:487 (1988). Thirty ul of phage eluted from the agarose plug (see Example 2) was used directly in each PCR reaction. Oligonucleotide primers, SEQ ID NO:3, (5'-CATCCCCATCTCCTCCACGCGGAA-3') and, SEQ ID NO: 4, (5'-TCGGTCGTCCGGCAGTACAATGGA-3') corresponding to sequences located approximately 100 bp on either side of the λgt11 EcoRI cloning site were used. The PCR reaction was performed using a Perkin Elmer Cetus PCR kit using 100 pmoles of primers in a total reaction volume of 100 ul. The reaction was incubated in a Perkin Elmer Cetus DNA Thermal cycler at 30 cycles with a 1 minute, 94° C. melting; 2 minute, 55° C. annealing and 3 minute, 72° C. polymerization steps.

Ten ul of each PCR reaction was electrophoresed in an TAE agarose gel. All clones produced a DNA fragment of about 1000 bp which was consistent with the anticipated size of c33c and flanking λgt11 regions (approximately 800 bp+200 bp). These PCR generated DNA fragments were eluted out of the gel using DEAE NA45 cellulose membrane, Dretzen et al., *Anal. Biochem.*, 112:295 (1981), followed by phenol/chloroform and ethanol precipitation. The flanking λgt11 DNA was removed by digestion, and electrophoresed on an TAE agarose gel. All three clones gave a 829 bp band consistent with the full length of c33c.

The DNA fragments were isolated and purified as described above. Approximately 0.5–1 ug of the PCR amplified c330 fragments with EcoRI termini were cloned into the EcoRI site of pUC19 (50 ng) using T$_4$DNA ligase. The ligated material was transformed into 50–100 ul of *E. coli* DH5a competent cells (Bethesda Research Labs, Bethesda, Md.) according to instructions. Transformation reactions were plated on LB ampicillin agar containing X-gal. Mini prep plasmid DNA of suspected recombinants were prepared using the alkaline lysis method, Birnhoim and Doly, *Nucleic Acids Res.*, 7:1513 (1979), digested with EcoRI, and electrophoresed in an TAE agarose gel to verify the presence of expected insert.

Double-stranded sequencing of the c33c containing pUC19 clones was performed with either the TaqTrack sequencing system (Promega, Madison, Wis. or Sequenase 2.0 US Biochemicals, Cleveland, Ohio). Four mg of alkali-denatured template and a forward primer (New England Biolab, Beverly, Mass. #1224 or reverse New England Biolab #1233) were annealed and subjected to dideoxy nucleotide sequencing. Partial sequencing of these clones from both ends confirmed that the HCV c33c region had been successfully cloned.

The DNA sequence from all 3 clones were identical, consequently only C33c-4A was further analyzed.

EXAMPLE 4

Construction of Desired c33c Sequence into λgt11

A complete c33c restriction endonuclease map was generated using the DNA STRIDER 1.1 program (Christian Marck, Department of Biology, Commission of Atomic Energy, France). Specific restriction sites were chosen to generate c33c gene fragments (FIG. 1). The criteria for choosing restriction sites were: 1) the sites were either unique or occurred infrequently in the c33c gene or the s accompanying vector (pUC19); and 2) provided fragments of approximately 100–180 bp in length. The DNA of c33c-4A clone isolated in Example 3 (c33c in pUC19). was digested (2–5 mg) with single or multiple restriction enzyme (Bethesda Research Labs, Gaithersburg, Md.; New England Biolabs, Beverly, Mass.) in a total volume of 20 ul, for at least 3 hours according to manufacturers' instructions. The restricted DNA was blunted-ended by adding 1 ul of a 2.5 mM dNTP mix and 1 ul T$_4$ DNA polymerase (New England Biolabs, Beverly, Mass.) and incubated at 12° C. for 15 minutes. The DNA was then extracted with phenol/chloroform followed by ethanol precipitation. EcoRI 5' phosphorylated linkers (Clontech, Palo Alto, Calif.) were ligated to the blunt-ended c33c restriction fragments to facilitate ligation into the EcoRI site of λgt11. EcoRI linkers of appropriate lengths were ligated to restore an open reading frame in phase with the Betagalactosidase gene of λgt11. One ug of EcoRI linkers and 2–5 ug of c33c restriction fragments were ligated with T$_4$DNA ligase in a total volume of 10 ul and incubated at 12° C. overnight. The ligation mixture was heat-inactivated at 65° C. for 15 minutes to destroy T$_4$DNA ligase activity, followed by digestion with EcoRI in a volume of 50–100 ul. DNA in the digestion reaction was size fractionated in a 1–2% agarose TAE preparative gel and the c33c fragment of expected size was eluted and purified using a Gene Clean Kit (Research Products Inc., Mount Prospect, Ill.). The purified DNA was then cloned into the λgt11, using the Protoclone λgt11 plus Packagene System (Promega, Madison, Wis.). Briefly, 0.5 ug (1 ul) of λgt11 dephosphorylated EcoRI arms was ligated to ug (2 ul) of c33c restriction fragment in a total volume of 5 ul at room temperature for 3 hours. Phage packaging extract (50 ul) was added to the mixture and incubated for an additional 2 hours at 22° C. The packaging extract was brought to a volume of 500 ul and 25 ul of chloroform was added as a preservative. The different λgt11 clones containing c33c fragment inserts that were generated are shown in FIG. 1. The inserts were subcloned into pUC19 and their DNA sequence determined to confirm their expected composition.

EXAMPLE 5

Immunoscreening of c33c Restrictions Fragments

The restriction fragments of c33c expressed in λgt11 were analyzed for serological activity by immunoscreening using procedures described in Example 2. The clones of FIG. 1 which contained the inserts of the correct DNA sequence were immunoscreened using a pool of three anti-HCV reactive specimens. These results are presented in Table 3. The clones were further immunoscreened with individual sera consisting of 10 anti-HCV c33c reactive sera and 7 c33c/non-reactive sera. The serological profile of this panel is shown in Table 4. The results indicate that the Ban II/EcoRI fragment contains one or more epitopes that is (are) recognized by all members of the panel that react with full length c33c antigen. The immunoreactivity of the panel members to c33c-4A full length reflects similar relative immunoreactivity determined with c33c RIBA test (Ortho Diagnostics, Raritan, N.J.). The complete sequence of the Ban II/EcoRI fragment is presented in FIG. 2.

TABLE 3

Characterization of c33c Constructs

| Construct | Size (AA) | Relative Reactivity (Pool) |
|---|---|---|
| Sca I[1,2] | 61 | – |
| Ava I[2] | 113 | ++ |
| Ban II[2] | 160 | ++ |
| Sac II[2] | 226 | +++ |
| c33c-4A | 261 | ++++ |
| Ava I Ban II | 47 | – |
| Ban II Sac II | 66 | – |
| Sac II Eco RI | 35 | – |
| Sca I Sac II | 165 | +++ |
| Ban II Eco RI | 102 | ++++ |

[1]This clone was not sequenced but presented a PCR fragment of the expected size.
[2]These clones contain EcoRI site at the 5' end of the insert.

TABLE 4

| | | Plaque Lift Immunoreactivity of c33c Constructs in λgt11 |
| | | SERA ID# |

| Clone | Size (AA) | Mixed 14 | Mixed 16 | Mixed 8 | Low 9 | Low 10 | D 9 | D 12 | D 13 | D 22 | DB 2453 | JL | 269 B | LS 1 | LS 3 | LS 5 | LS 7 | LS 12 |
|---|---|---|---|---|---|---|---|---|---|---|---|---|---|---|---|---|---|---|
| RIBA II c33c | 261 | 4 | 4 | 3 | 1 | 2 | – | – | 4 | 1 | 4 | – | 1 | – | – | – | – | – |
| c33c-4A | 261 | +++ | +++ | ++ | ++ | +++ | – | – | +++ | ++ | ++++ | ++ | +++ | – | – | – | – | – |
| Sac II | 226 | ++ | ++ | +ʷ | +. | ++ | – | – | ++ | + | +++ | + | ++ | – | – | – | – | – |
| Ban II | 160 | +/– | + | – | – | + | – | – | + | – | ++ | – | + | – | – | – | – | – |
| Ava I | 113 | ND | – | – | – | – | – | – | – | ++ | ND | ND | – | – | – | – | – | – |
| Sca I | 61 | – | – | – | – | – | – | – | – | – | – | – | – | – | – | – | – | – |
| Ava I Ban II | 47 | – | – | – | – | – | – | – | – | – | – | – | – | – | – | – | – | – |
| Ban II Sac II | 66 | – | – | – | – | – | – | – | – | – | – | – | – | – | – | – | – | – |
| Sac II Eco RI | 35 | – | – | – | – | – | – | – | – | – | – | – | – | – | – | – | – | – |
| Sca I Sac II | 165 | ++ | ++ | +ʷ | + | + | – | – | + | + | +++ | + | + | – | – | – | – | – |
| Ban II Eco RI | 101 | ND | ++ | ++ | ++ | ++ | – | – | ++ | ++ | ++++ | + | + | – | – | – | – | – |
| λgt11 | | – | – | – | – | – | – | – | – | – | – | – | – | – | – | – | – | – |

EXAMPLE 6

Production of Smaller Fragments c33c BAN II/ EcoRI By PCR Subsequent Immunoscreening Synthetic oligonucleotide primers were designed in the c33c HCV region to isolate smaller fragments by PCR. Additional bases at the 5' end and an EcoRI restriction site were added to the primers to facilitate cloning and correct in frame expression with λgt11 B-galactosidase.

The sequences of the primers were: (SEQ ID NOS:5, 6, and 7, nucleotides 5, 8, and 9, respectively, and SEQ ID NO:8 (includes nucleotides 1, 2, 3, 4, and 7.) (The EcoRI site is underlined.)

1 5'GCGCCGGAATTCCGTATTGCAGTCTATCACC-GAG-3' (SEQ ID NO:10)

2 5'GCGTATGAATTCTCCGTCACTGTGCCCCATC-CCAA-3' (SEQ ID NO:11)

3 5'GCGTATGAATTCAACATCGCCGCTGGTCGG-GAT-3' (SEQ ID NO:12)

4 5'GCGTATGAATTCGCTCTGTCCACCACCGGA-GAGAT-3' (SEQ ID NO:13)

5 5'GCGTATGAATTCCCAGTAGTGCCCCAGAG-CTTCCA-3' (SEQ ID NO:5)

7 5'GCGTATGAATTCGGTCATGAGGGCATCGGTT-3' (SEQ ID NO:14)

8 5'GCGTATGAATTCGGAGTGGCACTCGTCAC-AAAT-3' (SEQ ID NO:6)

9 5'GCGTATGAATTCAAGTTCCTTGCCGACGGC-3' (SEQ ID NO:7)

Primer pairs used for PCR: #1 and #2; #2 and #3; #1 and #4; #3 and #4; #2 and #7; #4 and #7; #5 and #8; #3 and #9; #1 and #9.

Figure 3:
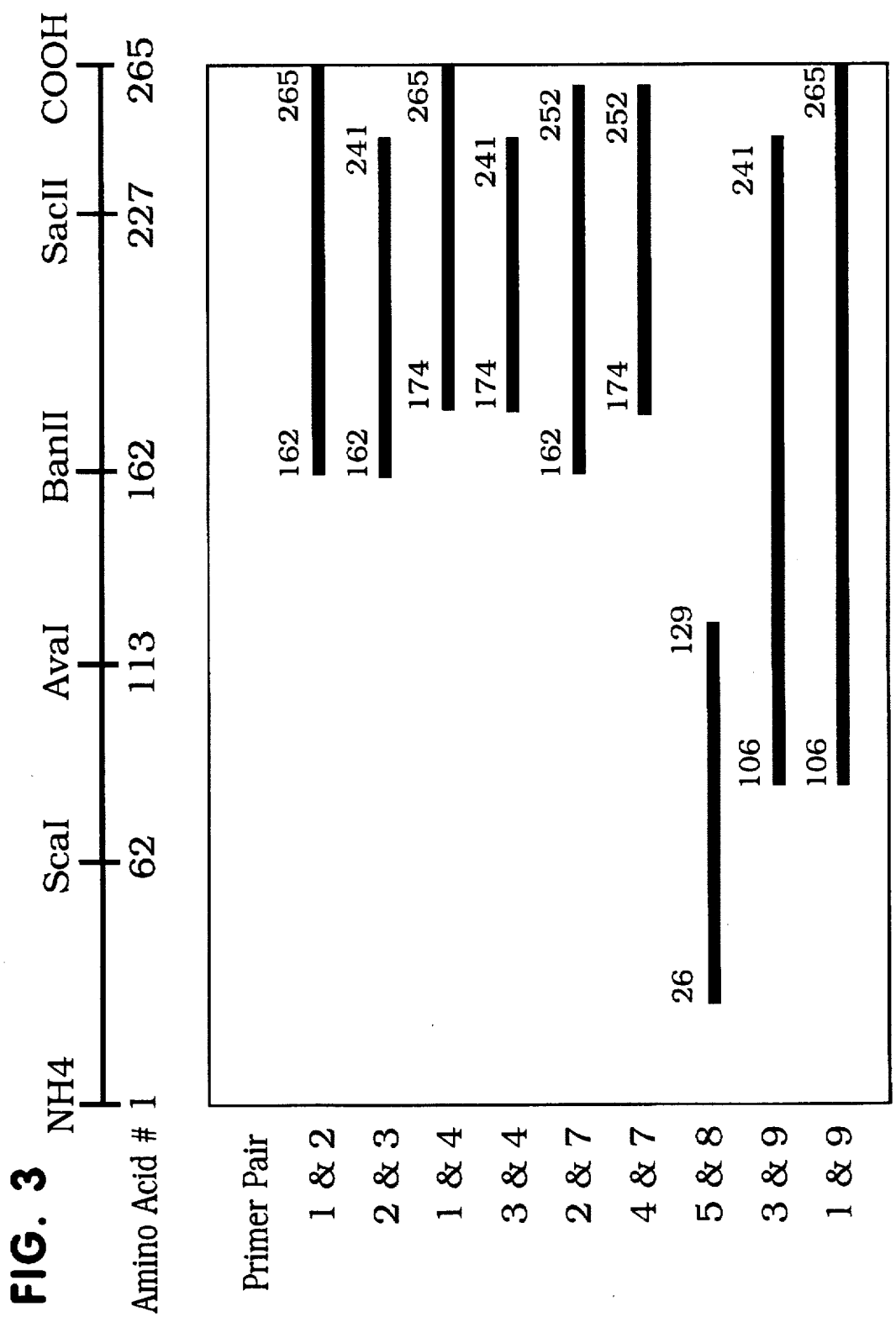
FIG. 3 is a nucleotide map showing the positions of various fragments amplified by the primer pairs indicated.

The location of viral gene product within the c33c region is shown in FIG. 3.

The PCR reaction was performed as described in Example 3 using 80 pmoles of each primer and 5 ng of pUC19 c33c-4A as a template. The correct sizes of the PCR products were verified concentrated from the gel matrix Gene Clean. The purified PCR products were then digested with EcoRI and cloned into λgt11 as described in Example 1 and 4. These clones were immunoscreened according to Example 2 using an anti-HCV a serum panel consisting of 9 c33c reactive members and 1 c33c non-reactive serum. The results (Table 5) indicate that cloned products smaller than Ban II/EcoRI product fail to react with all 9 members of the c33c reactive panel. These results demonstrate that the Ban II/EcoRI cannot be shorted by more than 12 amino acids at the 5' end or 13 amino acids at the 3' end without loss of immunoreactivity.

EXAMPLE 7

Cloning of BAN II/EcoRI c33 c Fragment into pGEX Plasmid Vector for Protein Expression and Protein Purification Ban II/EcoRI c33c DNA fragment was removed from the corresponding pUC19 clone by EcoRI digestion, size-fractionated on a 2% TAE agarose gel and purified by Gene Clean. This fragment was cloned into the EcoRI site of the expression vector pGEX-3Xa, Smith & Johnson, *Gene*, 67:31 (1988). This vector will express inserts in frame as a fusion with the C terminus of the 26 KD glutathione S-transferase (GST) protein from *Schistosoma japonicum*. The recombinant plasmid was then transformed into *E. coli* DH5a (Bethesda Research Labs, Gaithersburg, Md.) according to the manufacturer's protocol. The GST-c33c Ban II/EcoRI fusion gene was expressed and the protein was purified by the following modifications of the method described by Smith and Johnson, *Gene*, 67:31 (1988). Overnight cultures grown in LB broth containing 50 ug/ml ampicillin were diluted in 1:10 in fresh medium and grown 37° C. to an OD600 0.4. At that point Isopropyl-Beta-D-thiogalactopyranoside (IPTG) was added to a concentration of 0.1 mM. The culture was grown for an additional 2 hours at 37° C., cells were pelleted by centrifugation and resuspended in $^1\!/_{50}$ or $^1\!/_{100}$ culture volume of NTPBS (150 mM NaCl, 16 mM $Na_2HPO_4$, 4 mM $NaH_2PO_4$, pH 7.3). Cells were lysed on ice by sonication followed by addition of Triton X-100 to 1%. The lysate was centrifuged at 10,000×g for 5 minutes at 4° C. The supernatant of the centrifugation was mixed at room temperature on a rotator with $^1\!/_{10}$ volume of 50% glutathione agarose beads (Sulfur linkage, Sigma Chemical Co., St. Louis, Mo.) that had been prewashed and diluted in MTPBS. After a 2–3 minute adsorption, the agarose beads were collected by a 2 minute centrifugation at 500×g and the pellet was washed 3 times with MTPBS. The fusion protein was eluted from the beads by competition with 5 mM reduced glutathione (Sigma Chemical Co., St. Louis, Mo.) in 50 mM Tris-HCl pH 8.0 using 2×2 minute washes with 1 bead volume.

TABLE 5

Immunoreactivity Profile of Ban II/ EcoRI c33c Subclones

| Clone (Primer Pair) | D 12 | Mixed 14 | Low 10 | Low 9 | SERA ID# 2453 | Mixed 16 | 269B | JL | D 22 | D 13 |
|---|---|---|---|---|---|---|---|---|---|---|
| λgt11 | − | − | − | − | − | − | − | − | − | − |
| c33c | − | +++ | +++ | +++ | +++ | +++ | +++ | ++ | + | ++ |
| Ban II/ Eco RI | − | ++ | ++ | + | +++ | ++ | + | + | + | + |
| #2 & #3 | − | + | − | − | + | − | − | − | − | − |
| #1 & #4 | − | + | + | − | ++ | + | + | − | − | − |
| #3 & #4 | − | − | − | − | ++ | − | − | − | − | − |
| #2 & #7 | − | +/− | + | − | +++ | + | + | − | + | − |
| #4 & #7 | − | − | − | − | ++ | − | +/− | − | − | − |
| #5 & #8 | − | + | + | ++ | +++ | +++ | +/− | − | − | + |
| #3 & #9 | − | + | +/− | +/− | + | + | − | + | − | − |
| #1 & #9 | − | + | ++ | +/− | +++ | + | ++ | − | + | − |

EXAMPLE 8

Western Blot Immunoreactivity c33c BAN II/EcoRI Fusion Protein

Western blots were performed to determine the reactivity of the GST-c33c Ban II/EcoRI fusion protein purified in Example 7. The GST-c33c Ban II/EcoRI antigen was electrophoresed through a 12% SDS polyacrylamide preparative gel, Laemmli, Nature, 227:680 (1970), and transferred to Immobilon P (Millipore, Mass.) membrane using the Hoeffer TE 50 electro-transfer tanks as described by the manufacturer. The membrane was incubated with 5% NFDM solution in TBS for 30 minutes at room temperature and then cut into 3 mm strips. The strips were incubated individually with serum specimens diluted 1/100 in NFDM solution (46 anti-HCV c33c reactive sera and 29 c33c non-reactive sera) overnight at room temperature. The strips were washed 4×5 minutes in 3M NaCl/50 mM Tris pH 8.0/0.01M NaN₃ solution, followed by a rinse in alkaline phosphatase goat anti-human antibody. The strips were then incubated with washed, and incubated with substrate as described in Example 2.

The results of the Western Blot analysis of the GST-c33c Ban II/EcoRI fusion protein are shown in Table 6.

The c33c Ban II/EcoRI fusion protein was immunoreactive with all (46/46) of the c33c reactive sera. These HCV specimens have been well characterized and range from very low anti-HCV titer specimens to high titer ones. None of non-reactive c33c specimens were found to be reactive 0/29. These results demonstrate that the Ban II/EcoRI fragment of c33c retain all of the immunoreactivity of full length c33c protein.

EXAMPLE 9

Immunoreactivity of GST-BAN II/EcoRI Using a Paramagnetic Microparticle Enzyme Immunoassay The immunoreactivity of OST-Ban II/EcoRI fusion protein and the full-length c33c protein were compared with a paramagnetic microparticle enzyme immunoassay (MP assay). This assay detects anti-HCV by utilizing a paramagnetic solid phase particles with HCV antigens coated on their surface. Paramagnetic microparticles (MP) were obtained from Baxter Diagnostics, Inc., Pandex, Mundelein, Ill. They consisted of a fluorescent polystyrene paramagnetic core and a polystyrene surface. All particle preparations were characterized by a narrow size distribution (average diameter was 4.5 um). The GST-Ban II/EcoRI and c33c viral gene products were purified as described in Example 7. The full-length c33c protein was expressed with a 16 amino acid leader in the pET5a system, Studier and Moffatt, J. Mol. Biol. 189:113 (1986). The viral antigens at 400 ug protein/ml of 0.1M acetate buffer pH 5.0 were coated passively onto MP (2.5% w:v) by gentle mixing of the antigen with MP overnight at room temperature. The MP were then washed extensively with PBS (20 mM sodium phosphate, 150 mM NaCl, pH 7.4) using centrifugation (5000 rpm, 5 minutes). The antigen coated MP were diluted in PBS to a working concentration of 0.025% (w.v).

TABLE 6

Western Blot Immunoreactivity of Ban II/Eco RI Fragment Compared to Full-Length c33c

| | | c33c + | c33c − |
|---|---|---|---|
| Ban II/ Eco RI | + | 46 | 0 |
| | − | 0 | 29 |

Specimens were diluted 1:100 (dilution buffer: 15% newborn calf sera, 500 nM NaCl, 100 mM Tris-HCl, 0.3% Nonidet P-40, pH 7.4), and 50 ul was placed into each well of a black plastic microtitre plate. Twenty ul of MP (0.025% w:v) were added to each well and allowed to incubate at 42° C. for 30 minutes. Particles in each well were then washed 5 times with PBS containing 0.05% Tween-20 using a magnetic field to keep the particles at the bottom of each well during the washing steps. Fifty ul of goat anti-human Ig (H+L) beta-galactosidase conjugate (American Qualex, La Mirada, Calif.) diluted 1:800 in conjugate diluent (8% newborn calf sera, 50 mM Tris-HCl, 200 mM NaCl and 1 mM MgCl2, pH 7.4) was then added to each well and incubated at 42° C. for 15 minute. The plate was then washed as described above. Fifty ul of substrate (4-methyl umbelliferyl beta-galactoside, MUG: 0.5 mM MUG, 20 mM Tricine, 0.05% Tween-20, ph 8.5) was added to each well and product fluorescence was measured (365 nm excitation and 450 nm emission) at timed intervals (2 minutes and 14 minutes). fluorescence values were converted into nM coumarin values using dilutions of coumarin as a standard curve. A kinetic value for substrate turnover (the amount of coumarin in nM generated over a 12 minute period) was determined using Quattro Pro (Borland International, Scotts Valley, Calif.) spreadsheet software program. The dynamic range of kinetic values was 0 to 5,000 nM coumarin. A preliminary algorithm for cutoff calculation was established by testing random volunteer blood donor samples as well as panels of serial serum samples from patients who were monitored during seroconversion. The algorithm (nM coumarin of positive calibrator×0.75) resulted in a cutoff of approximately 200–300 nM coumarin.

Results in Table 7 demonstrate that using MP assay all sera immunoreactive to the full length c33c antigen are also reactive to the Ban II/EcoRI product. Stronger reactivity of the full-length c33c with some specimens reflects the fact that the MP assay was not optimized for the Ban II/EcoRI viral product. Approaches to optimize the Ban II/EcoRI product into the MP assay include removing the GST fusion from Ban II/EcoRI by factor X cleavage, Smith and Johnson, *Gene*, 67:31 (1988), cloning of Ban II/EcoRI into pET 5a, Studier and Moffatt, *J. Mol. Biol.*, 189:113 (1986), or coating the viral product on the solid phase in a different manner.

TABLE 7

IMMUNOREACTIVITY OF BAN II/ECORI pGEX FUSION USING A PARAMAGNETIC MICROPARTICLE IMMUNOASSAY*

Antigen

| Specimen ID | Ban II/EcoRI | c33c Full Length |
|---|---|---|
| Low 1 | 1198 | 1314 |
| Low 3 | 1391 | 1209 |

TABLE 7-continued

IMMUNOREACTIVITY OF BAN II/ECORI pGEX FUSION USING A PARAMAGNETIC MICROPARTICLE IMMUNOASSAY*

Antigen

| Specimen ID | Ban II/EcoRI | c33c Full Length |
|---|---|---|
| Low 6 | 3177 | 5000 |
| Mixed 1 | 1099 | 5000 |
| Mixed 2 | 3472 | 5000 |
| Mixed 5 | 5000 | 5000 |
| Mixed 6 | 1174 | 5000 |
| Mixed 8 | 5000 | 5000 |
| Mixed 20 | 5000 | 5000 |
| QCR 9 | 5000 | 5000 |
| QCR 10 | 5000 | 5000 |
| QCR 11 | 5000 | 5000 |
| QCR 12 | 669 | 700 |
| QCR 13 | 5000 | 5000 |
| QCR 14 | 5000 | 5000 |
| QCR 15 | 5000 | 5000 |
| QCR 16 | 5000 | 5000 |
| 269B | 460 | 493 |
| Neg pool 9 | 39 | 40 |

*Results are expressed as nM coumarin. Values greater than 300 are reactive.

What is claimed is:

1. An immunodominant polypeptide encoded by the hepatitis C NS 3 gene consisting of
   a recombinant protein consisting of the carboxy-terminal 102 amino acid fragment of the c33c region of NS3.

2. An assay for detecting antibodies specific to the c33c region of the hepatitis C NS3 protein comprising contacting a solid support coated with a recombinant protein consisting of the carboxy-terminal 102 amino acid fragment of said c33c region with a sera or plasma specimen incubating said specimen and said recombinant protein coated solid support for a time sufficient to permit antibodies specific for said fragment contained in said specimen to bind to said coated solid support separating said bound antibodies from unbound antibodies, and detecting the antibodies so bound.

3. The assay of claim 2 wherein said solid support is paramagnetic particles.

4. The assay of claim 2 wherein said separation step is carried out by magnetic concentration of paramagnetic particles, washing the pellet so concentrated, and resuspending in a buffered solution.

5. The assay of claim 2 wherein said antibody detection utilizes an anti-human antibody conjugated to signal-generating means.

6. An assay for detecting antibodies specific to the c33c region of hepatitis C NS3 protein comprising electrophoresing a recombinant protein consisting of the carboxy-terminal 102 amino acid fragment of the c33c region of the hepatitis C NS3 protein, transferring said electrophoresed recombinant protein to a membrane contacting said protein with a patient specimen containing antibodies to the c33c protein, contacting with enzyme-conjugated anti-human antibodies, washing, and developing with substrate, wherein antibodies specific to the c33c region are detected.

7. The assay of claim 6 wherein said solid support is paramagnetic particles.

8. The assay of claim 6 wherein said separation step is carried out by magnetic concentration of paramagnetic particles, washing the pellet so concentrated, and resuspending in a buffered solution.

9. The assay of claim 6 wherein said antibody detection utilizes an anti-human antibody conjugated to signal-generating means.

10. A synthetic peptide consisting of the sequence as shown in SEQ ID NO:9.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

CCGGCCGGCC GAATTTCACA CGTATTGCAG TCTATCA      3 7

( 2 ) INFORMATION FOR SEQ ID NO:2:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

```
CGCGCGCGCG GAATTCGTGG ACTTTATCCC TGTGGA                                36
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
CATCCCCATC TCCTCCACGC GGAA                                            24
```

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
TCGGTGGTCC GGCAGTACAA TGGA                                            24
```

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GCGTATGAAT TCCCAGTAGT GCCCCAGAGC TTCCA                                35
```

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GCGTATGAAT TCGGAGTGGC ACTCGTCACA AAT                                  33
```

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
GCGTATGAAT TCAAGTTCCT TGCCGACGGC                                      30
```

( 2 ) INFORMATION FOR SEQ ID NO:8:

( i ) SEQUENCE CHARACTERISTICS:
    ( A ) LENGTH: 306 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..306

( x i ) SEQUENCE DESCRIPTION: SEQ ID NO:8:

```
GTC ACT GTG CCC CAT CCC AAC ATC GAG GAG GTT GCT CTG TCC ACC ACC    48
Val Thr Val Pro His Pro Asn Ile Glu Glu Val Ala Leu Ser Thr Thr
 1               5                  10                  15

GGA GAG ATC CCT TTT TAC GGC AAG GCT ATC CCC CTC GAA GTA ATC AAG    96
Gly Glu Ile Pro Phe Tyr Gly Lys Ala Ile Pro Leu Glu Val Ile Lys
            20                  25                  30

GGG GGG AGA CAT CTC ATC TTC TGT CAT TCA AAG AAG AAG TGC GAC GAA   144
Gly Gly Arg His Leu Ile Phe Cys His Ser Lys Lys Lys Cys Asp Glu
        35                  40                  45

CTC GCT GCA AAG CTG GTT GCT TTG GGC ATC AAT GCC GTG GCT TAC TAC   192
Leu Ala Ala Lys Leu Val Ala Leu Gly Ile Asn Ala Val Ala Tyr Tyr
    50                  55                  60

CGC GGT CTT GAC GTG TCC GTC ATC CCG ACC AGC GGC GAT GTT GTC GTC   240
Arg Gly Leu Asp Val Ser Val Ile Pro Thr Ser Gly Asp Val Val Val
65                  70                  75                  80

GTG GCA ACC GAT GCC CTC ATG ACC GGC TAT ACC GGC GAC TTC GAC TCG   288
Val Ala Thr Asp Ala Leu Met Thr Gly Tyr Thr Gly Asp Phe Asp Ser
                85                  90                  95

GTG ATA GAC TGC AAT ACG                                           306
Val Ile Asp Cys Asn Thr
            100
```

( 2 ) INFORMATION FOR SEQ ID NO:9:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Val Thr Val Pro His Pro Asn Ile Glu Glu Val Ala Leu Ser Thr Thr
 1               5                  10                  15

Gly Glu Ile Pro Phe Tyr Gly Lys Ala Ile Pro Leu Glu Val Ile Lys
            20                  25                  30

Gly Gly Arg His Leu Ile Phe Cys His Ser Lys Lys Lys Cys Asp Glu
        35                  40                  45

Leu Ala Ala Lys Leu Val Ala Leu Gly Ile Asn Ala Val Ala Tyr Tyr
    50                  55                  60

Arg Gly Leu Asp Val Ser Val Ile Pro Thr Ser Gly Asp Val Val Val
65                  70                  75                  80

Val Ala Thr Asp Ala Leu Met Thr Gly Tyr Thr Gly Asp Phe Asp Ser
                85                  90                  95

Val Ile Asp Cys Asn Thr
            100
```

( 2 ) INFORMATION FOR SEQ ID NO:10:

( i ) SEQUENCE CHARACTERISTICS:

(A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCGCCGGAAT TCCGTATTGC AGTCTATCAC CGAG     34

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCGTATGAAT TCTCCGTCAC TGTGCCCCAT CCCAA     35

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GCGTATGAAT TCAACATCGC CGCTGGTCGG GAT     33

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCGTATGAAT TCGCTCTGTC CACCACCGGA GAGAT     35

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCGTATGAAT TCGGTCATGA GGGCATCGGT T     31